US00PP13015P2

(12) United States Plant Patent
Klemm

(10) Patent No.: US PP13,015 P2
(45) Date of Patent: Sep. 24, 2002

(54) NEW GUINEA IMPATIENS PLANT NAMED 'OSLO'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 2 days.

(21) Appl. No.: 09/876,938

(22) Filed: Jun. 11, 2001

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of New Guinea Impatiens plant named 'Oslo', characterized by its large dark pink-colored flowers; freely flowering habit with flowers positioned above or beyond the foliage; compact, mounded and outwardly spreading plant habit; very freely branching growth habit; dark green-colored leaves; and good weather tolerance.

1 Drawing Sheet

BOTANICAL CLASSIFICATION

*Impatiens hawkeri* cultivar Oslo.

BACKGROUND OF THE INVENTION

The present Invention relates to a new and distinct cultivar of New Guinea Impatiens plant, botanically known as *Impatiens hawkeri*, and hereinafter referred to by the cultivar name Oslo.

The new Impatiens is a product of a planned breeding program conducted by the Inventor in Stuttgart, Germany. The objective of the breeding program is to develop new freely branching Impatiens cultivars with compact plant habit, numerous flowers and interesting flower and foliage colors.

The new Impatiens originated from a cross made by the Inventor during the fall of 1996 of a proprietary *Impatiens hawkeri* selection identified as code number M 347, not patented, as the female, or seed parent, with a proprietary *Impatiens hawkeri* selection identified as code number N 177, not patented, as the male, or pollen parent. The cultivar Oslo was discovered and selected by the Inventor as a flowering plant within the progeny of the stated cross in controlled environment in Stuttgart, Germany, in May, 1997.

Asexual reproduction of the new cultivar by terminal cuttings taken at Stuttgart, Germany, since July, 1997, has shown that the unique features of this new Impatiens are stable and reproduced true to type in successive generations.

SUMMARY OF THE INVENTION

The following traits have been repeatedly observed and are determined to be the unique characteristics of 'Oslo'. These characteristics in combination distinguish 'Oslo' as a new Impatiens cultivar and distinguish it from other known Impatiens cultivars:

1. Large dark pink-colored flowers.
2. Freely flowering habit with flowers positioned above or beyond the foliage.
3. Compact, mounded and outwardly spreading plant habit.
4. Very freely branching growth habit.

5. Dark green-colored leaves.
6. Good weather tolerance.

Plants of the new Impatiens differ from plants of the parent selections primarily in plant growth habit, leaf color and flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Oslo' grown during the fall and winter in Stuttgart, Germany, in a 12-cm container for about 14 weeks after planting a rooted cutting.

DETAILED BOTANICAL DESCRIPTION

The cultivar Oslo has not been observed under all possible environmental conditions. The phenotype may vary somewhat with variations in environment such as temperature, light intensity, daylength, water status and/or fertilizer type or rate, without, however, any variance in genotype. The following observations and measurements describe plants grown in Stuttgart, Germany during the fall and winter, under commercial practice in a glass-covered greenhouse. Plants used in the following description were grown in 12-cm containers for about 14 weeks after planting rooted cuttings. During the production period, day and night temperatures ranged from 20 to 22° C. In the following description, color references are made to The Royal Horticultural Society Colour Chart except where general terms of ordinary dictionary significance are used.

Botanical classification: *Impatiens hawkeri* cultivar Oslo.
Commercial classification: New Guinea Impatiens cultivar Oslo.
Parentage:

*Female parent.*—Proprietary *Impatiens hawkeri* selection identified as code number M 347, not patented.

*Male parent.*—Proprietary *Impatiens hawkeri* selection identified as code number N 177, not patented.

Propagation:

*Type cutting.*—Terminal cuttings.

*Time to initiate roots.*—About 10 days at 20° C.

*Time to produce a rooted cutting.*—About 21 days at 20° C.

*Root description.*—Numerous, cream-white, fibrous and freely branching.

Plant description:

*General appearance.*—Compact, mounded and outwardly spreading plant habit.

*Growth and branching habit.*—Very freely branching, about 10 lateral branches per plant develop without pinching, that is, removal of the terminal apices. Moderately vigorous growth habit; densely foliated.

*Crop time.*—To produce a finished flowering plant in a 12-cm container: About 12 weeks from a rooted cutting.

*Plant height.*—About 16 cm.

*Plant spread.*—About 32 cm.

*Lateral branch description.*—Length: About 9 cm. Diameter: About 6 mm. Internode length: About 3 cm. Texture: Smooth, glabrous. Color: 143C; anthocyanin at nodes, 178A.

*Foliage description.*—Arrangement: Opposite or in whorls. Length, mature leaves: About 10 cm. Width, mature leaves: About 3.5 cm. Shape: Lanceolate, oblong. Apex: Acuminate. Base: Attentuate. Margin: Serrulate with fine ciliation. Texture, both surfaces: Smooth, glabrous, leathery. Venation pattern: Pinnate. Color: Young foliage, upper surface: 143A, glossy. Young foliage, lower surface: 139D. Fully expanded foliage, upper surface: 139A, glossy. Fully expanded foliage, lower surface: 139D. Venation, upper surface: Midvein: 182B. Lateral veins: 143C. Venation, lower surface: Midvein: 194C. Lateral veins: 143A. Petiole: Length: About 2 cm. Diameter: About 3 mm. Texture: Smooth, glabrous. Color: Upper surface: 182B. Lower surface: 194C.

Flower description:

*Flower type and flowering habit.*—Single, large, oval-shaped dark pink-colored flowers. Freely flowering, usually about 5 flowers and flower buds per lateral branch. Flowers positioned above and beyond the foliage and typically face upward or outward. Flowers flat when fully opened. Flowers last about 10 to 14 days on the plant depending on environmental conditions. Petals self-cleaning; gynoecium persistent. Flowers not fragrant. Flowering indeterminate and continuous.

*Flowering season.*—Year-round under greenhouse conditions. In the garden, flowering from spring until fall.

*Flower length.*—About 6.4 cm.

*Flower width.*—About 5.7 cm.

*Flower depth (thickness).*—About 1 cm.

*Flower buds.*—Rate of opening: From flower bud to fully open flower, typically about 5 to 7 days depending on temperature. Length: About 1.7 cm. Diameter: About 9 mm. Shape: Ovoid. Texture: Smooth, glabrous. Color, just before opening: 52B.

*Petals.*—Quantity: Five per flower, imbricate. Length: Banner petal: About 2.7 cm. Lateral petals: About 3 cm. Lower petals: About 3.7 cm. Width: Banner petal: About 4.4 cm. Lateral petals: About 2.4 cm. Lower petals: About 3.3 cm. Shape: Roughly cordate. Apex: Emarginate. Base: Rounded to acute. Margin: Entire. Texture: Smooth; satiny. Color: When opening and fully opened, upper surface: 52B, center and towards base, slightly darker than 52B; fading to 55A with subsequent development. When opening and fully opened, lower surface: 55A.

*Spur.*—Length: About 5.1 cm. Diameter: At flower: About 2 mm. At apex: About 0.5 mm. Texture: Smooth, glabrous. Color: 63A.

*Peduncles.*—Length: About 4.5 cm. Diameter: About 1.5 mm. Strength: Strong, flexible. Aspect: About 45° from the stem. Texture: Smooth, glabrous. Color: 147C.

*Reproductive organs.*—Androecium: Stamen number: Five fused at anthers, filaments free, hooded. Anther shape: Obovate. Anther length: About 4 mm. Anther width: About 3 mm. Anther color: 57D. Amount of pollen: Abundant. Pollen color: 157A. Gynoecium: Pistil number: One. Pistil length: About 6 mm. Stigma shape: Columnar, five-segmented. Stigma color: 158C. Style color: 158C. Ovary color: 141A.

*Seed development.*—Seed development has not been observed.

Disease/pest resistance: Plants of the new Impatiens have not been observed to be resistant to pathogens or pests common to Impatiens.

Weather tolerance: In Stuttgart, Germany, plants of the new Impatiens have been observed to be tolerant to wind and rain and tolerate temperatures from 12 to 30° C.

It is claimed:

1. A new and distinct cultivar of New Guinea Impatiens plant named 'Oslo', as illustrated and described.

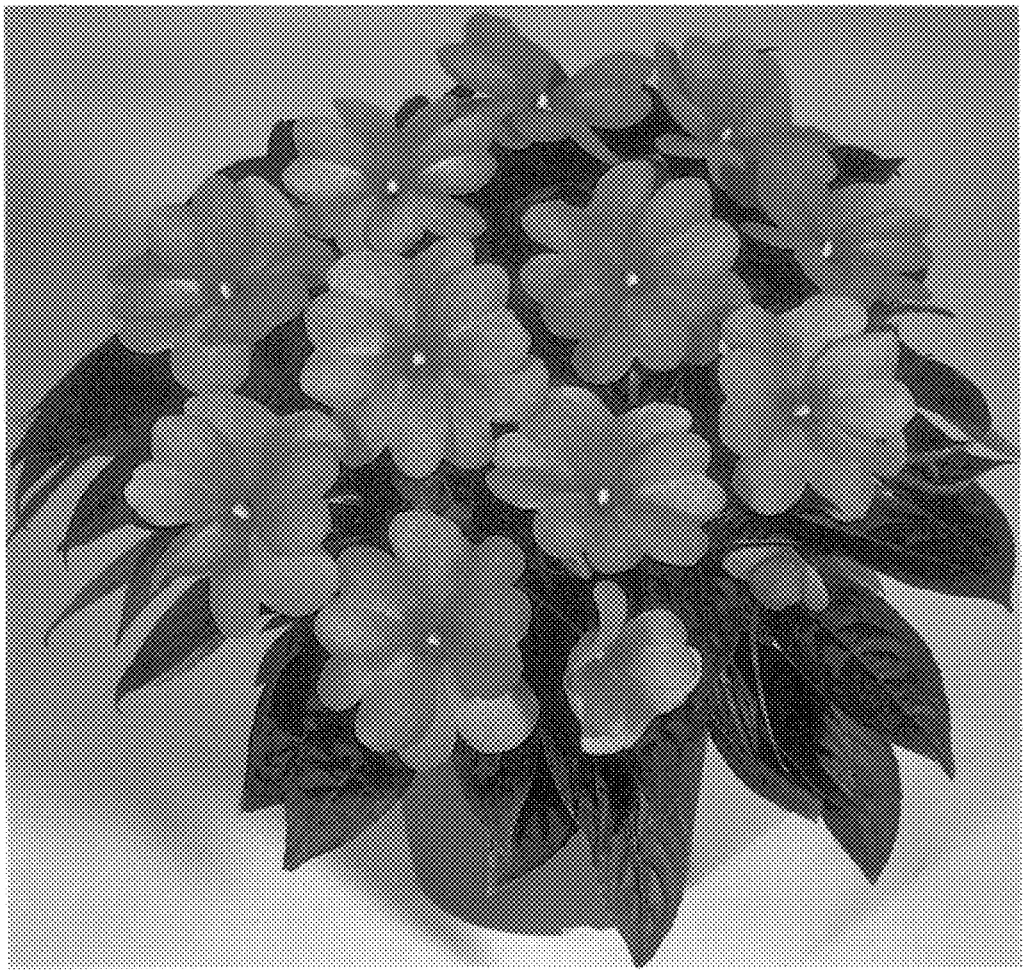

* * * * *